United States Patent
Penelle

(10) Patent No.: US 6,890,486 B2
(45) Date of Patent: May 10, 2005

(54) MIP/QCM SENSORS FOR HIGH SENSITIVITY-FAST SENSING OF SMALL MOLECULES IN SOLUTION

(75) Inventor: Jacques Penelle, Hadley, MA (US)

(73) Assignee: University of Massachusetts, Amherst, MA (US)

( * ) Notice: Subject to any disclaimer, the term of this patent is extended or adjusted under 35 U.S.C. 154(b) by 197 days.

(21) Appl. No.: 09/915,723

(22) Filed: Jul. 26, 2001

(65) Prior Publication Data

US 2003/0049173 A1 Mar. 13, 2003

(51) Int. Cl.[7] ............................ G01N 7/00; G01N 27/00; G01N 33/48; G01N 35/00; G01R 29/22
(52) U.S. Cl. .................. 422/82.01; 422/50; 422/58; 422/83; 422/68.1; 436/43; 436/149; 324/727
(58) Field of Search ........................ 422/50, 58, 68.1, 422/83, 98, 82.01; 436/43, 149, 116; 324/727, 439; 428/422; 430/269; 526/201; 264/330

(56) References Cited

U.S. PATENT DOCUMENTS

| | | | | | |
|---|---|---|---|---|---|
| 5,587,273 | A | * | 12/1996 | Yan et al. | 430/269 |
| 5,630,978 | A | * | 5/1997 | Domb | 264/330 |
| 5,958,787 | A | * | 9/1999 | Schonfeld et al. | 436/116 |
| 5,959,050 | A | * | 9/1999 | Mosbach et al. | 526/201 |
| 5,990,684 | A | * | 11/1999 | Merrill | 324/439 |
| 6,500,547 | B1 | * | 12/2002 | Potyrailo | 428/422 |

* cited by examiner

*Primary Examiner*—Jill Warden
*Assistant Examiner*—Brian Sines
(74) *Attorney, Agent, or Firm*—William B. Ritchie

(57) ABSTRACT

The present invention relates to quartz crystal microbalance sensors using molecular imprinting polymerization technology, providing for continuous on-line monitoring of water-borne organic contaminants.

7 Claims, 1 Drawing Sheet

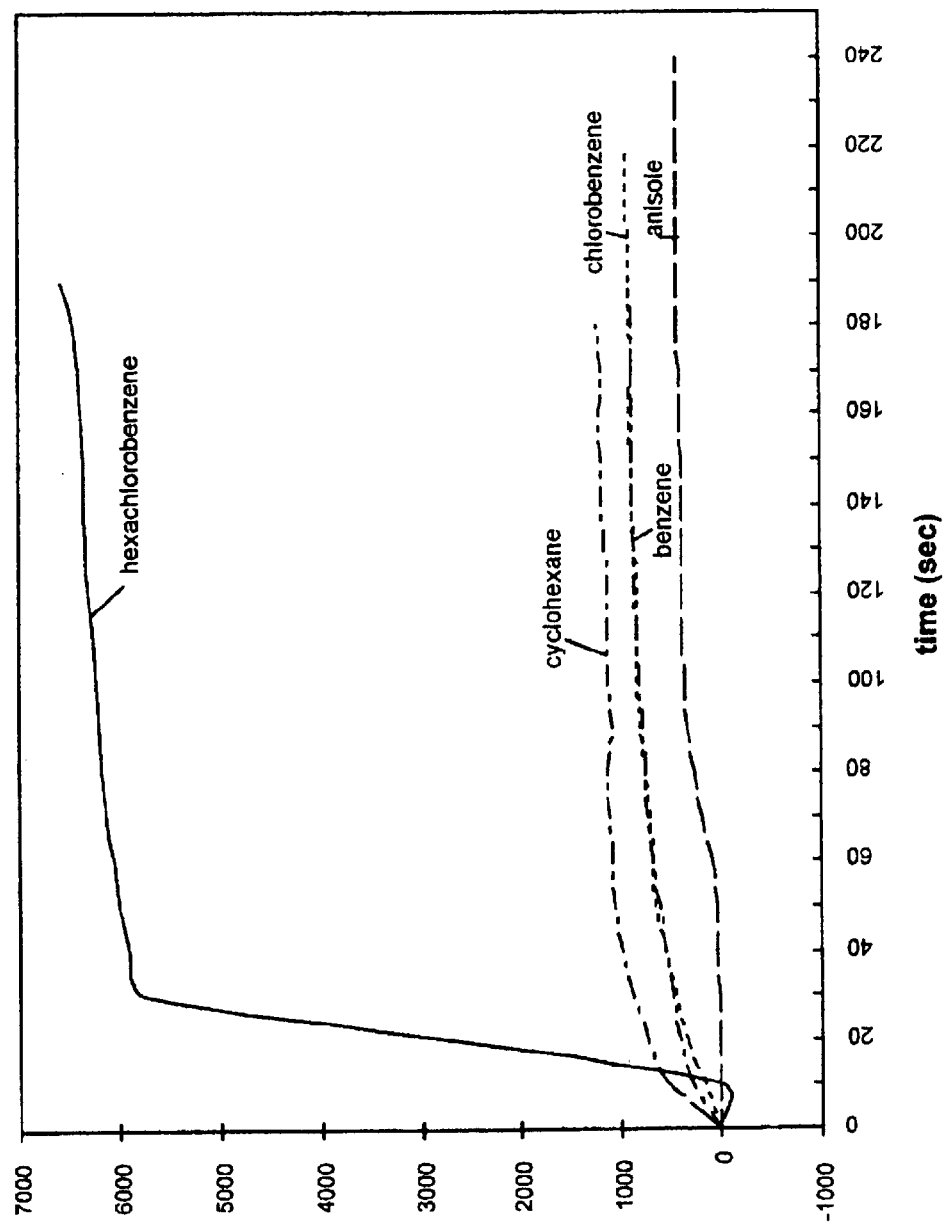
DRAWING

MIP/QCM SENSORS FOR HIGH SENSITIVITY-FAST SENSING OF SMALL MOLECULES IN SOLUTION

FIELD OF THE INVENTION

This invention relates to the field of molecularly imprinted polymers (MIPs) and, in particular, to their use in quartz crystal microbalance (QCM) sensor devices.

BACKGROUND OF THE INVENTION

Designing sensors for pollutants has long been, and still is, an important technological challenge. U.S. Pat. No. 5,990,684, issued to Merrill (the '684 patent), which patent is herein incorporated by reference in its entirety, is directed to a "method and apparatus for continuously monitoring an aqueous flow to detect and quantify ions." The method involves providing a conduit having at least one ion collection portion, disposing the aqueous flow through the conduit, attracting target ions to the ion collection portion such that they are bonded to the ion collection portion, and detecting a contaminant, or contaminants, based upon a predetermined property of the plurality of target ions bonded to the ion collection portion. In the preferred embodiment of the method, the predetermined property is a conductivity of the target ions, and the detecting step involves measuring a change in conductivity of the collection portion as ions are bonded and comparing that conductivity to a predetermined conductivity. The apparatus includes a conduit into which an ion collection portion is disposed, a sensor that senses ions collected on the ion collection portion and sends a signal corresponding to a value of a predetermined property of the ions, and a microprocessor in communication with the sensor and programmed to process the signal and determine the presence of the at least one contaminant based upon the processed signal.

A particularly useful molecular sensing technology is based on quartz crystal microbalances (QCMs), a family of very sensitive and inexpensive sensors that produce a frequency shift in quartz crystal vibration when molecules interact with the sensor surface. These sensors can be used in both the gas and liquid phases, and generate a signal that is generally proportional to the concentration of the interacting molecules. Gas phase QCMs are commercially used in the electronic industry.

In the liquid phase, QCMs have been coupled to antibodies, allowing for the selective sensing of the antibody conjugate. More recently, a technique called "molecular imprinting" has also been used. Molecular imprinting polymerization (MIP) is a molecular technology that allows for the selective recognition of targeted molecules by cross-linked polymers. This technique consists of coating a cross-linked templated polymeric layer to the QCM surface.

Though recent, the molecular imprinting technique is known in the art. For example, U.S. Pat. No. 5,630,978 discloses a method for preparing mimics of a wide variety of drugs and other biologically active molecules using molecular imprinting techniques. Additionally, U.S. Pat. No. 5,959,050 is directed to a molecularly imprinted support formed from at least two distinct acrylic monomers and at least one imprinted molecule. What is needed in the art, therefore, is the use of MIP techniques in QCM-based sensors for continuous on-line monitoring of harmful, water-borne organic contaminants.

SUMMARY OF THE INVENTION

The present invention combines MIP molecular recognition technology, which allows for the selective recognition of targeted molecules by cross-linked polymers, with the sensitivity offered by QCM sensors. The MIP/QCM sensors provide high sensitivity and fast sensing for small molecules in a solution, such as aqueous organic pollutants. This allows for continuous on-line monitoring of contaminants.

The process of combining MIP techniques with QCMs includes choosing the proper monomers and on-chip polymerization of imprinting agents to provide MIP-functionalized QCM probes. In experimentation with the present invention, a MIP/QCM sensor has been fabricated that can recognize hexachlorobenzene with an excellent response time and at concentrations consistent with applications in pollution control.

Therefore, it is an aspect of this invention to apply MIP molecular recognition technology to QCM sensors.

It is another aspect of the invention to provide on-chip polymerization of imprinting agents to provide MIP/QCM sensors.

It is a further aspect of the invention to provide continuous on-line monitoring for specified contaminates.

It is a further aspect of the invention to provide MIP/QCM sensors that are efficient and sensitive to detecting specified pollutants.

These aspects of the invention are not mean to be exclusive and other features, aspects, and advantages of the present invention will be readily apparent to those of ordinary skill in the art when read in conjunction with the appended claims.

BRIEF DESCRIPTION OF THE DRAWINGS

The Drawings illustrates QCM measurements in aqueous solutions.

DETAILED DESCRIPTION OF THE INVENTION

As disclosed in the incorporated '684 patent at column 4, lines 57–65, an apparatus for the continuous monitoring of contaminants in solution includes a conduit into which an ion collection portion is disposed, a sensor that senses ions collected on the ion collection portion and sends a signal corresponding to a value of a predetermined property of the ions, and a microprocessor in communication with the sensor and programmed to process the signal and determine the presence of the at least one contaminant based upon the processed signal.

In preferred embodiments of the present invention, QCM sensors are used to detect the collected molecules and ions. Said molecules are attracted to the QCMs by molecularly imprinted polymers programmed to recognize the specific molecules. The collection and recognition of these molecules is then translated into a signal that a microprocessor interprets as the presence of specific contaminants.

The first phase of the invention is monomer choice and synthesis. Several acrylic monomers containing aromatic linkers were synthesized under the assumption that the aromatic groups, in particular the electron-rich groups, would induce favorable electronic interactions. These π-interactions are the only directional attractive forces that can be used for molecules like chlorinated aromatics or polyaromatic molecules.

The structures of six monomers (1–2, 4–6, and 8) synthesized for this invention are indicated in the following figures along with the synthetic schemes used to obtain them. Detailed experimental procedures follow.

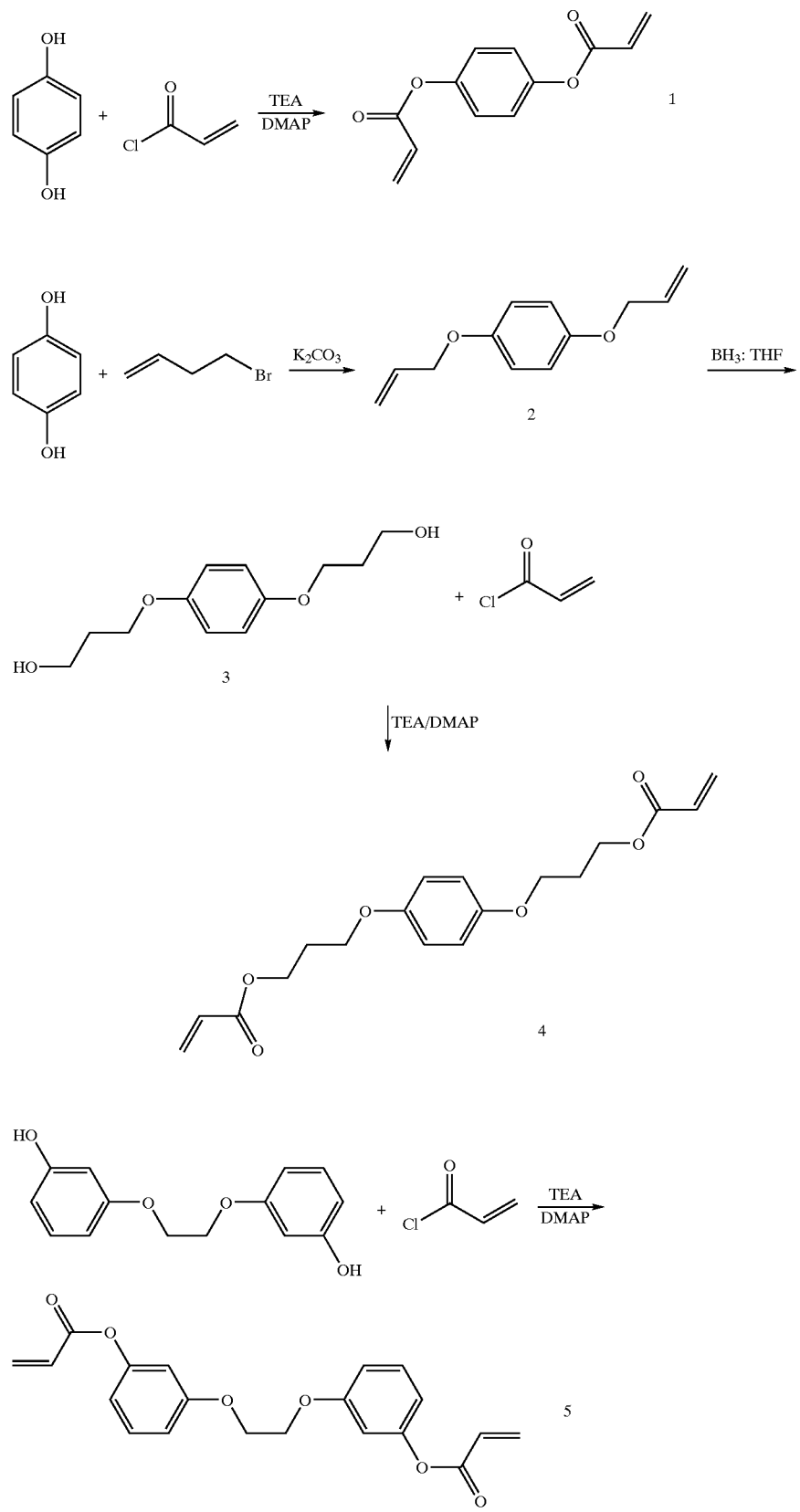
FIG. 1. Synthetic routes for acrylic monomers

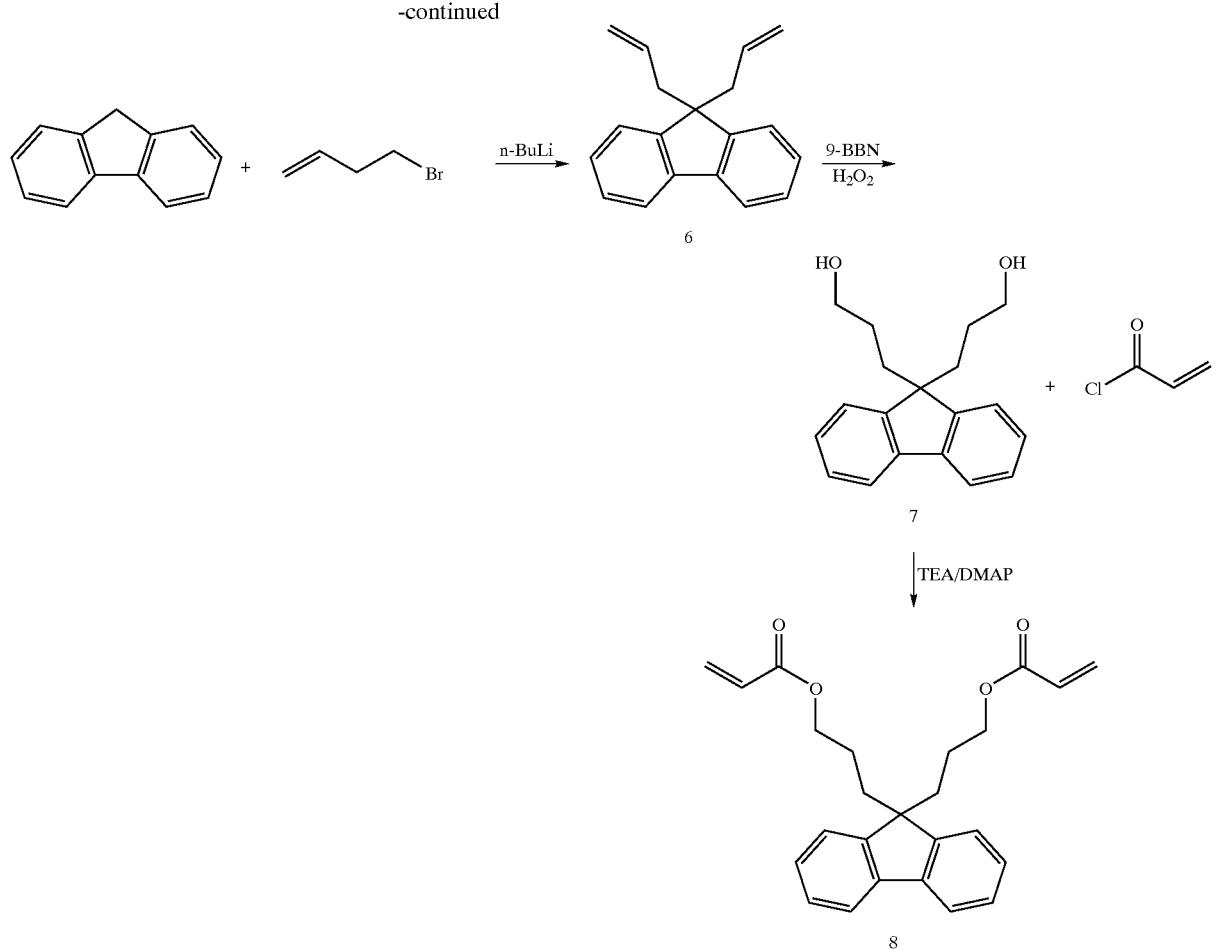

All reactions were carried out in oven-dried glassware under Argon unless otherwise indicated. Tetrahydrofuran and dichloromethane were distilled over Na/benzophenone and CaH$_2$ respectively prior to use. All $^1$H NMR was measured at 200 MHz in CDCl$_3$. 9,9 diallyl fluorene was prepared according to Waymouth et al. *J. Am. Chem. Soc.*, 1994, 116(5), 1845–54.

Preparation of (1)

To a solution of hydroquinone (1.0 g, 9.1 mmol), TEA (1.6 mL, 2.0 mmol), and DMAP (cat.) in CH$_2$Cl$_2$ (50 mL), acrolyl chloride (2.8 mL, 2.0 mmol) was added slowly and stirred overnight. The reaction mixture was then washed with brine (3×30 mL), the organic layer was collected, dried over MgSO$_4$, and passed through a short path of silica to remove any unreacted hydroquinone. Solvent was removed by rotary evaporation to give 1.45 g (73%) product. $^1$H NMR (δ, ppm) 5.9 (CH, 1H, d, J=15 Hz), 6.5 (CH, 1H, s), 6.8 (CH, 1H, s), 7.1 (Ar, 2H, s).

Preparation of (2), Diallyl Hydroquinone

A solution of hydroquinone (500 mg, 4.5 mmol) in acetone (20 mL) was degassed with Ar for 10 minutes. K$_2$CO$_3$ (1.88 g, 13.6 mmol) and allyl bromide (1.17 mL, 13.6 mmol) were added and the solution was refluxed overnight. The brown solution was then cooled and filtered. Acetone was removed by rotary evaporation. The resulting oil was purified by flash column chromatography (2:1 hexane/ethyl acetate) to afford a white solid (1.0g, 89%). $^1$H NMR (δ, ppm) 1.4 (t, J=6 Hz), 2.0 (CH$_2$, q, J=9 Hz), 4.8 (CH$_2$, q, J=9 Hz), 5.3 (CH$_2$, J=10 Hz).

Preparation of (3)

(2) (500 mg, 2.6 mmol) was dissolved in THF (10 mL) and cooled in a dry ice bath. BH$_3$:THF (1M solution, 5.26 mL) was added drop wise over 15 minutes. The solution was allowed to warm to room temperature and stirred for three hours. A 1:1 mixture of 3M NaOH and 30% H$_2$O$_2$ (10 mL) was added and the solution was stirred for two days. The milky white solution was washed with brine (3×10 mL) and purified by flash column chromatography (1:3 hexane/ethyl acetate) to afford a white powder (503 mg, 85%). $^1$H NMR (δ, ppm) 1.8 ppm (OH, t, J=6 Hz), 2.0 (CH$_2$, q, J=9 Hz), 3.8 (CH$_2$, q, J=9 Hz), 4.3 (CH$_2$, q, J=10 Hz), 6.8 (Ar, s).

Preparation of (4)

To a solution of (3) (50 mg, 0.2 mmol) and TEA (0.06 mL, 4 mmol) in CH$_2$Cl$_2$ (10 mL), acryloyl chloride (0.04 mL, 0.4 mmol) was added and stirred overnight. The reaction mixture was washed with brine (3×10 mL). The organic layer was collected and dried over MgSO$_4$. The solvent was removed by rotary evaporation and the resulting oil purified by flash column chromatography (5:1 (v:v) hexane/ethyl acetate) to give a white crystalline powder (43 mg, 64%). $^1$H NMR (δ, ppm) 1.8 ppm (OH, t, J=6 Hz), 2.0 (CH$_2$, q, J=9 Hz), 3.8 (CH$_2$, q, J=9 Hz), 4.3 (CH$_2$, q, J 10 Hz), 6.8 (Ar, s).

Preparation of (5) and (8)

This esterification was done as in the preparation of (1). Yields: 87% and 68%, respectively. $^1$H NMR (5) (δ, ppm) 4.1 (t, 4H CH$_2$O, J=22 Hz), 5.9 (CH, 1H, d, J=15 Hz), 6.5 (CH, 1H, s), 6.8 (CH, 1H, s), 7.1 (Ar, m, 2H), 7.8 (Ar, m, 1H).

Preparation of (6)

This was synthesized according to literature procedures, Knight, K. S., Wang, D., Waymouth, R. M., Ziller, J. *J. Am. Chem. Soc.*, 1994, 116, 1845–54.

Preparation of (7)

Hydroboration procedure was identical to that of (3). Yield: 81%.

Repeated attempts to synthesize bisacrylamide (9) proved unsuccessful. The five conditions used to synthesize (9) from 1,4-phenylenediamine and acryloyl chloride are outlined in FIG. 2.

linked acrylic networks on the gold-made surface of a QCM probe.

The on-chip cross-linked coatings synthesized and studied for this invention were all obtained by fast UV-photopolymerization of a thin liquid film containing a commercial bis- or trisacrylate (tripropyleneglycol diacrylate (TPGDA) or trimethylopropane triacrylate (TMPTA)), a reactive diluent (benzyl methacrylate), a photoinitiator (2-benzyl-2-dimethylamino-4'-morpholino-butyrophenone (Irgacure 369), azo-bis(isobutyronitrile (AIBN) or tetraeth-

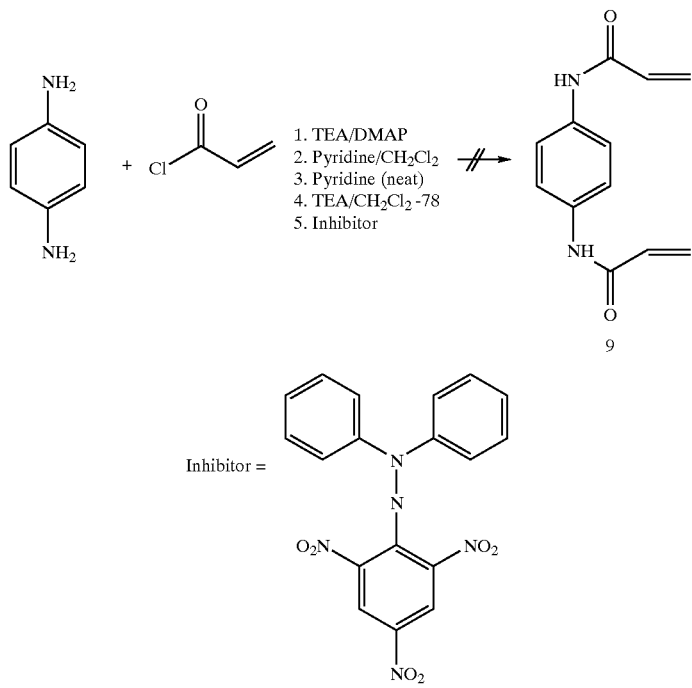

FIG.2 Attempts to synthesize bisacrylamide

Shown in FIG. 3, the acrylic-capped n-alkanethiol (10) was also synthesized as a monomer able to modify the gold surface by making so-called "self-assembling monolayers" (SAMs).

ylthiuram disulfide (TETD)) and various additives aimed at improving the adhesion of the final cross-linked polymer on the gold surface. The initial thin liquid film was obtained by spin coating a few microliters of a solution containing the

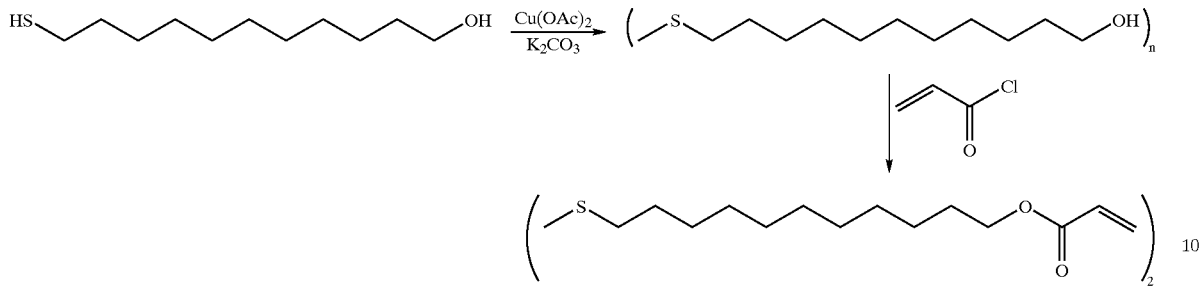

FIG. 3 Acrylic-capped n-alkanrthiol

Once proper monomers have been chosen, the next phase includes on-chip polymerization of imprinting agents to provide MIP-functionalized QCM probes. Several approaches were explored for the synthesis of heavily crossreagents diluted in tetrahydrofuran (THF) or dichloromethane. The film had previously been deposited on the gold surface of the chip. The light source used in these experiments has a very high intensity allowing most of the photopolymerization to occur in less than 20 seconds. The exact amounts of each monomer/reagent and detailed experimental conditions are provided in the annex.

Preliminary experiments with 'simple' acrylic networks obtained by photoirradiation of TPGDA and benzyl methacrylate indicated a very poor adhesion of the film on the metallic surface: the film peeled off instantaneously after immersion in either dichloromethane or acetonitrile. This behavior was both expected and surprising. Surprising because claims made in the recent literature imply that conditions can be found to obtain good adhesion of acrylic or styrenic polymers on a gold surface. Expected as this problem has a long history in polymer science and engineering and is still considered today as one of the key problem in UV-curing on metallic surfaces (UV-cured paintings or plastic coatings on cars are traditional examples). The physics of the phenomenon is complex in its details, but the rationale for the poor adhesion is well known and understood: the polymer film shrinks during the curing while the underlying metallic substrate does not, generating a very large amount of stress at the interface.

Strategies that were successively considered to solve this problem include:
1. use of acrylic acid as a co-monomer,
2. use of itaconic acid as a co-monomer,
3. modification of the gold surface with a thiol-capped acrylic monomer able to self-assemble on the surface,
4. use of tetraethylthiuram disulfide as a photoinitiator or chain-transfer agent,
5. use of triacrylate (TMPTA) as the multifunctional monomer,
6. use of bis(dehydroalanine) (11) (DBHA) as the multifunctional monomer.

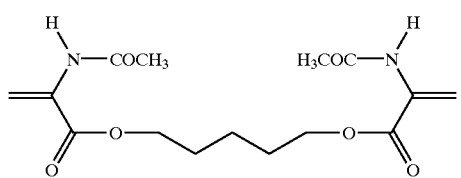

FIG. 4 Bis(dehydroalanine).

The rationale for the above curing conditions is as follows:
(1 and 2). Introduce carboxylic acid for improved adhesion with the gold surface.
This strategy has been recently used in a MIP experiment (Haupt, K.; Noworyta, K.; Kuter, W. *Anal. Commun.*, 1999, 36, 391–393).
(3 and 4). Introduction of sulfur-containing groups for improved adhesion with the gold surface.
(5). Different stress buildup in the film.
(6). Monomer was available and had been shown to improve adhesion on several substrates.

The coatings obtained using strategies 1–5 showed adhesion properties. However, the use of monomer (11) is the preferred method, especially in adhering to metal surfaces.

Initial experiments on the acrylic network showed that enough adhesion can be obtained to remove the template (hexachlorobenzene) from the imprinted matrix. After removal of the template, QCM measurements were performed with aqueous solutions of hexachlorobenzene (1.3 to $2.8 \times 10^{-8}$ M), benzene ($5 \times 10^{-8}$ M), cyclohexane ($5 \times 10^{-8}$ M), chlorobenzene ($5 \times 10^{-8}$ M) and anisole ($5 \times 10^{-8}$ M). The results are shown in the Drawing.

The results can be summarized as follows. The sensor displays selectivity with regard to cyclohexane, benzene, chlorobenzene and anisole. A signal at least six times stronger is obtained for hexachlorobenzene than for the other molecules. The response time is excellent; a stable signal is obtained after less than 20–30 seconds. A MIP/QCM sensor based on a non-imprinted polymer coating (fabricated in the absence of hexachlorobenzene as a template) did not display any signal. Preliminary experiments demonstrated that the designed sensor works as efficiently under acidic (pH=5), neutral (pH=7), and basic conditions (pH=9).

Although the present invention has been described with reference to certain preferred embodiments thereof, other versions are readily apparent to those of ordinary skill in the art. Therefore, the spirit and scope of the appended claims should not be limited to the description of the preferred embodiments contained herein.

What is claimed is:

1. A quartz crystal microbalance sensor using molecularly imprinted polymers comprising:
   a quartz crystal microbalance sensor having a surface;
   a matrix of synthesized monomers coating said surface; and
   a multifunctional monomer for use as an adhesive wherein said multifunctional monomer is bis (dehydroalanine) comprising the formula:

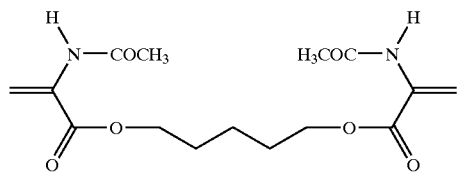

wherein said multifunctional monomers adheres a polymerized matrix to said surface of said sensor, and said matrix is a molecularly imprinted polymer.

2. The sensor as claimed in claim 1, wherein said synthesized monomers comprise acrylic monomers having aromatic linkers.

3. A quartz crystal microbalance sensor using molecularly imprinted polymers comprising:
   a quartz crystal microbalance sensor having a surface;
   a matrix of acrylic monomers polymerized to coat said surface of said quartz microbalance sensor; and
   a multifunctional monomer comprising bis (dehydroalanine) of the structure

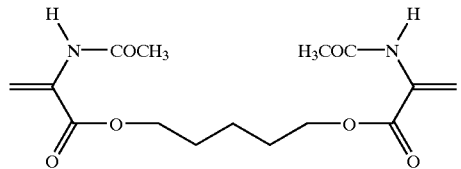

wherein said bis(dehysroalanine) adheres a polymerized matrix to said surface of said sensor, and wherein said matrix is molecularly imprinted.

4. An apparatus for detecting at least one contaminant in a solution, said apparatus comprising:
   a conduit;
   a molecularly imprinted polymer to attract said contaminant, said molecularly imprinted polymer adhered with an adhesive which is bis(dehydroalanine) having the structure

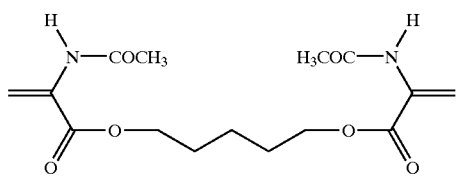

a quartz crystal microbalance sensor positioned within said conduit for sensing said contaminant attracted by said molecularly imprinted polymer such that said molecularly imprinted polymer is affixed to said quartz crystal microbalance sensor via said adhesive;
wherein said sensor sends a signal indicating said contaminant is present in said solution.

5. The apparatus as claimed in claim 4 further comprising a microprocessor in communication with said sensor, said microprocessor being programmed to process said signal and determine the presence of said contaminant based upon the processed signal.

6. The apparatus as claimed in claim 4 further comprising a multifunctional monomer for use as an adhesive, wherein said multifunctional monomer adheres said molecularly imprinted polymer to said sensor.

7. The apparatus as claimed in claim 6 wherein said molecularly imprinted polymer is programmed to attract a contaminant selected from the group consisting of hexachlorobenzene, cyclohexane, chlorobenzene, benzene, and anisole.

* * * * *

UNITED STATES PATENT AND TRADEMARK OFFICE
CERTIFICATE OF CORRECTION

PATENT NO. : 6,890,486 B2
DATED : May 10, 2005
INVENTOR(S) : Jacques Penelle, Vincent M. Rotello and Kanad Das It is certified that error appears in the above-identified patent and that said Letters Patent is hereby corrected as shown below:

<u>Title page,</u>
Item [75], Inventors, should read
-- Jacques Penelle
   Vincent M. Rotello
   Kanad Das --.

Signed and Sealed this

Sixth Day of September, 2005

JON W. DUDAS
*Director of the United States Patent and Trademark Office*